United States Patent [19]

Golub et al.

[11] Patent Number: 5,258,371
[45] Date of Patent: Nov. 2, 1993

[54] METHOD TO REDUCE CONNECTIVE TISSUE DESTRUCTION

[75] Inventors: Lorne M. Golub; Nangavarum S. Ramamurthy, both of Smithtown; Thomas F. McNamara, Port Jefferson; Robert A. Greenwald, Melville, all of N.Y.; Tsutomu Kawai, Kurashiki, Japan; Takashi Hamasaki, Kurashiki, Japan; Michiya Shimamura, Kurashiki, Japan; Goro Kobayashi, Kurashiki, Japan; Tetsuo Takigawa, Kurashiki, Japan; Hisashi Iwata, Nagoya, Japan

[73] Assignee: Kuraray Co., Ltd., Osaka, Japan

[21] Appl. No.: 891,554

[22] Filed: May 29, 1992

[51] Int. Cl.$^5$ .................................................. A61K 31/65
[52] U.S. Cl. ..................................... 514/152; 514/825
[58] Field of Search ........................................ 514/152

[56] References Cited

U.S. PATENT DOCUMENTS

| | | | |
|---|---|---|---|
| 4,666,897 | 5/1987 | Golub et al. | 514/152 |
| 4,704,383 | 11/1987 | McNamara et al. | 514/152 |
| 4,925,833 | 5/1990 | McNamara et al. | 514/152 |
| 4,935,411 | 6/1990 | McNamara et al. | 514/152 |
| 4,935,412 | 6/1990 | McNamara et al. | 514/152 |

OTHER PUBLICATIONS

Collier et al., "Evaluation of the Effects of Antiarthritic Drugs on the Secretion of Proteoglycans by Lapine Chondrocytes Using a Novel Assay Procedure", *Annals of the Rheumatic Disease* 48: 372-381 (1989).

Ramamurthy et al., "Diabetes Increases Collagenase Activity In Extracts of Rat Gingiva and Skin", *J. Periodontal Res.*, 18: 23-30 (1983).

Golub et al., "Minocycline Reduces Gingival Collagenolytic Activity During Diabetes", *J. Periodontal Res.*, 18: 516-526 (1983).

Golub et al., "Tetracyclines Inhibit Tissue Collagenase Activity", *J. Periodontal Res.*, 19: 651-655 (1984).

Yanagimura et al., "Collagenase Activity in Gingival Crevicular Fluid", *J. Dent. Res.*, 68 (Spec. Issue), 1691 (1989).

Golub et al., "Low-dose Doxycycline Therapy: Effect on Gingival and Crevicular Fluid Collagenase Activity in Humans", *J. Periodontal Res.*, 25: 321-330 (1990).

(List continued on next page.)

*Primary Examiner*—Leonard Schenkman
*Attorney, Agent, or Firm*—Hoffmann & Baron

[57] ABSTRACT

Provided is a method of treating humans or animals suffering from a condition or disease characterized by excessive collagen destruction, which comprises administering to said human or animal an effective amount of a 12a-deoxytetracycline represented by the following general formula

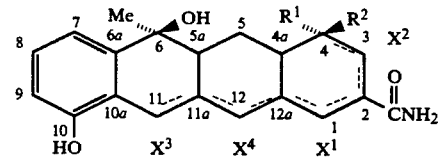

The method is effective in the treatment of various articular diseases characterized by excessive collagen destruction.

5 Claims, No Drawings

OTHER PUBLICATIONS

Perry et al., Letters to the Editor, *Cornea*, 3, 75 (1984).

Perry et al., "Systemic Tetracyclines in the Treatment of Noninfected Corneal Ulcers: A Case Report and Proposed New Mechanism of Action", *Ann. Ophthalmol.*, 17: 742–744 (1985).

Panayi et al., "Minocycline in the Treatment of Patients with Reiter's Syndrome", *Clin. Exp. Rheumatol.*, 7: 100 (1989).

Greenwald et al., "Tetracyclines Inhibit Human Synovial Collagenase In Vivo and In Vitro", *J. Rheumatol.*, 14: 28 (1987).

Breedveld et al., "Minocycline Treatment for Rheumatoid Arthritis: An Open Dose Finding Study", *J. Rheumatol.*, 17: 43 (1990).

Golub et al., "A Non-antibacterial Chemically-modified Tetracycline Inhibits Mammalian Collagenase Activity", *J. Dent. Res.*, 66: 1310 (1987).

Rifkin et al., "Effect of a Chemically-Modified Tetracycline (CMT) on Bone Resorption in Organ Culture: Preliminary Observations", *J. Cell Biol.*, 105 Abstracts, Abstr. No. 1223 p. 216a (1987).

Greenwald et al., "Direct Detection of Collagenase and Gelatinase in Periarticular Tissue from Adjuvant Arthritic Rats: Inhibition by Tetracyclines and Potential Amelioration of Bone Destruction", *The 36th Annual Meeting Orth Res. Soc.*, Abstract p. 268 (1990).

Mitscher, "Chemical Transformations of the Tetracycline Family", Chapter 6, *The Chemistry of Tetracyclines*, Marcel Dekker, Publishers, N.Y. (1978).

Green et al., "Chemistry of the Tetracycline Antibiotics. II. Bromination of Dedimethylaminotetracyclines", *J. Am. Chem. Soc.*, 82: 3946 (1960).

Green et al., "Chemistry of the Tetracycline Antibiotics. III. 12a-Deoxytetracyline", *J. Am. Chem. Soc.*, 82: 3950 (1960).

METHOD TO REDUCE CONNECTIVE TISSUE DESTRUCTION

BACKGROUND OF THE INVENTION

1. Field of the Invention

The present invention relates to a method for treating diseases characterized by connective tissue destruction and, more specifically, to a method for treating articular diseases, characterized by destruction of collagen which is a major constituent of connective tissues.

2. Description of the Prior Art

A variety of diseases are characterized by inflammation and connective tissue destruction. For treatment of these diseases, anti-inflammatory drugs have been used in most cases. In particular, non-steroidal anti-inflammatory drugs (hereinafter referred to as "NSAIDs") have been used for the purpose of suppressing pain and inflammation. The NSAIDs inhibit cyclooxygenase in metabolism of arachidonic acid present in the inflamed sites, thereby inhibiting prostaglandin synthesis. The NSAIDs are therefore considered to have direct analgesic and anti-inflammatory activities.

Immunomodulators are used for suppressing development of articular diseases. Where the conditions have become worse, adrenocorticoids, gold compounds, immunosuppressants and the like are used. Long-term use of adrenocorticoids however induces osteoporosis, while other agents have limited affects.

There has been interest in recent years in developing new drugs that will act by mechanisms different from those of the drugs listed above. A number of studies have been conducted to obtain drugs which will suppress destruction of articular tissues. In the course of the studies, it has been discovered that matrix metallo-proteinases, such as collagenase, play an important role in destroying connective tissue [Drugs Fut., 15 495 (1990)]. Antibiotic tetracyclines, such as tetracycline, minocycline and doxycycline, or their salts such as hydrochlorides (hereinafter these compounds are sometimes referred to as "tetracyclines") are known to have a broad antibacterial spectrum. Their activities other than that of an antibiotic nature have also been studied, and in 1983 a research group in State University of New York reported the anti-collagenolytic activity of minocycline in periodontal diseases [J. Periodontal Res., 18, 516 (1983)]. Since then, with the progress of studies on various diseases characterized by collagen destruction, tetracyclines have been studied for clinical application to treat these diseases. Thus, there have been reported treatment with tetracyclines for the following: periodontitis [J. Periodontal Res., 19, 651 (1984)] and J. Dent. Res., 68 (Spec. Issue), 1691 (1989)]; J. Periodontal Res., 25: 321–330 (1990); Corneal Ulcer [Cornea, 3, 75 (1984) and Ann. Ophthalmol., 17, 742 (1985)]; Reiter disease and Lyme disease [Clin. Exp. Rheumatol., 7, 100 (1989) and Annual Internal Med., 99, 22 (1983), respectively] and rheumatoid arthritis [J. Rheumatol., 14, 28 (1987)].

It has also been reported as a result of clinical testing of minocycline on patients suffering from rheumatoid arthritis that appreciable effects were observed 4 months after the start of administration [J. Rheumatol., 17, 43 (1990)].

As a result of knowledge regarding the collagenase-inhibiting activity of tetracyclines, efforts have been made to synthesize tetracycline derivatives. The research group in State University of New York has reported that chemically modified tetracyclines, such as 4-dedimethylaminotetracycline (hereinafter sometimes referred to as "DMAT"), are useful in treatments for rheumatoid arthritis, periodontal diseases and other diseases which require a long-term administration of treating drugs. [See U.S. Pat. No. 4,704,383 (Japanese Patent Application Laid-open No. 243023/1986)]. It has been found that DMAT compares favorably to tetracyclines with respect to collagenase inhibition, suppression of bone resorption, and the like, without the same antibacterial activity [J. Dent. Res., 66, 1310 (1987); J. Cell Biol., 105 Abstracts, abstr. No. 1223 p. 216a (1987) and The 36th Annual Meeting Orth. Res. Soc., abstract p. 268 (1990)].

In 1991, the research group in State University of New York reported that treatment with a combination of a chemically modified tetracycline having anti-collagenase activity but no antibacterial activity, such as DMAT, and an NSAID, such as flurbiprofen, suppressed bone-loss and proved to be effective for tissue-destroying diseases such as rheumatoid arthritis [U.S. patent application Ser. No. 07/445,410 (Japanese Patent Application Laid-open No. 227931/1991)].

Although NSAIDs, which produce analgesic and anti-inflammatory effects by inhibiting prostaglandin synthesis, are effective in suppressing pain and inflammation in articular diseases, they are not known as a remedy for suppressing or retarding the tissue-destructive progress of diseases. NSAIDs now widely used cause gastro-intestinal disorder resulting from inhibition of prostaglandin synthesis.

Accordingly, an object of the present invention is to provide a method of treating humans or animals suffering from a condition or disease characterized by connective tissues destruction, which comprises administering to said human or animal an effective amount of a non-antimicrobial tetracycline derivative or its pharmaceutically acceptable salts having excellent anti-collagenase activity and little toxicity or almost no side effects and being usable in a long-term therapy.

This object as well as other objects and advantages of the present invention will be apparent to those skilled in the art from the following detailed description.

SUMMARY OF THE INVENTION

The present invention provides a method for treating humans or animals suffering from a condition or disease characterized by connective tissue destruction, which comprises administering to said human or animal an effective amount of a 12a-deoxytetracycline represented by the following general formula (1)

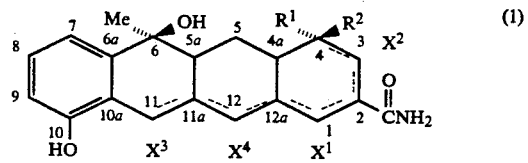

wherein $R^1$ represents a hydrogen atom or a dimethylamino group, $R^2$ represents a hydrogen atom or forms a double bond with the carbon atom in the C-3 position, $X^1$, $X^2$, $X^3$ and $X^4$ each represents a hydroxyl group or an oxo group and the broken lines drawn in places mean that there may be present a carbon-carbon double bond or a double bond formed by $X^1$, $X^2$, $X^3$ or $X^4$ and a ring-forming carbon atom in each of the places, the number of the bonds present in the places of the broken lines being 4 with the following conditions:

where $X^1$ represents a hydroxyl group, either one of C12a-C1 bond or C1-C2 bond is a double bond;

where $X^2$ represents a hydroxyl group, either one of C2-C3 bond or C3-C4 bond is a double bond;

where $X^3$ represents a hydroxyl group, C11-C11a is a double bond; and where $X^4$ represents a hydroxyl group, either one of C11a-C12 bond or C12-C12a bond is a double bond; with the limitation that said C1-C2 bond and said C2-C3 bond, said C11-C11a bond and said C11a-C12 bond, or said C12-C12a bond and C12a-C1 cannot be double bonds at the same time; and where $X^1$ represents an oxo group, said C12a-C1 bond and C1-C2 bond are each a single bond, where $X^2$ represents an oxo group, said C2-C3 bond and C3-C4 bonds are each a single bond, where $X^3$ represents an oxo group, said C11-C11a bond is a single bond, and where $X^4$ represents an oxo group, said C11a-C12 bond and C12-C12a bond are each a single bond;

or its pharmaceutically acceptable salts (hereinafter the 12a-deoxytetracycline or its pharmaceutically acceptable salts are sometimes referred to as "tetracycline derivatives").

DETAILED DESCRIPTION OF THE PREFERRED EMBODIMENTS

The 12a-deoxytetracyclines used in the present invention are 12a-deoxytetracycline (hereinafter sometimes referred to as "DOTC"), i.e., those of the formula (1) with $R^1$ being a dimethylamino group, and 4-dedimethylamino-12a-deoxytetracycline (hereinafter sometimes referred to as "DODMAT"), i.e., those of the formula (1) with $R^1$ being a hydrogen atom, of which DODMAT are more preferred.

DOTC comprise isomers represented by, for example, the following formulas

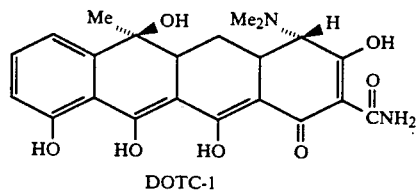

DOTC-1

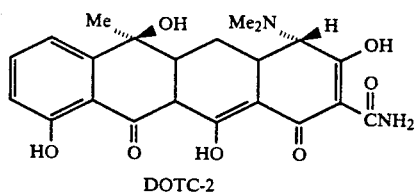

DOTC-2 and

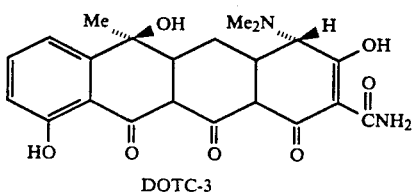

DOTC-3 while DODMAT comprise isomers represented by, for example,

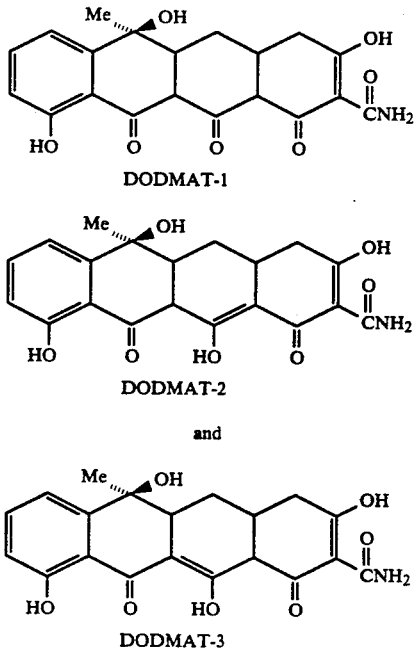

DODMAT-1

DODMAT-2 and

DODMAT-3

Examples of pharmaceutically acceptable salts of 12a-deoxytetracycline are salts with an acid such as hydrochloric acid, sulfuric acid, phosphoric acid, lactic acid, tartaric acid, maleic acid, fumaric acid, oxalic acid, malic acid, succinic acid, oleic acid or palmitic acid; salts with the hydroxide or carbonate of an alkali metal or alkali earth metal such as sodium, potassium, calcium or aluminum; and salts with triethylamine, benzylamine, diethanolamine, t-butylamine, dicyclohexylamine, arginine or the like.

These 12a-deoxytetracyclines are known compounds, being described in a) J. Am. Chem Soc., 82 745 (1960), b) J. Am. Chem. Soc., 82, 3946 (1960) and c) J. Am. Chem. Soc., 82, 3950 (1960).

The reference a) describes isomers represented by the above formulas DOTC-1 and DOTC-2, while c) describes one represented by the formula DOTC-3. The reference b) describes an isomer represented by the formula DODMAT-1 which might have a structure as shown by DODMAT-2.

The 12a-deoxytetracyclines can be synthesized according to the processes described in the above literature. DODMAT can be obtained by reducing a DMAT represented by the following formula

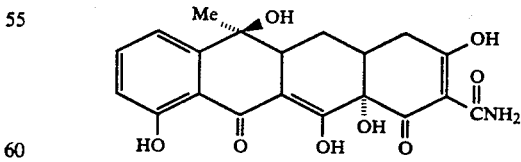

with zinc in an aqueous ammonia.

The pharmaceutically acceptable salts of the 12a-deoxytetracycline are prepared by utilizing known salt formation reactions.

Mixtures of DODMAT-2 and DODMAT-3 as obtained in Synthesis Example 1, as well as DOTC as obtained in Synthesis Example 2 described later herein, have excellent anti-collagenase activity, as shown in a later-described Test Example.

As shown in the later-described Test Example, a mixture of DODMAT-2 and DODMAT-3 showed significant suppression of destruction of articular cartilages using rabbit osteoarthritis models.

Toxicological studies have shown the low toxicity of the tetracycline derivatives used in the present invention, with almost no side effects observed after a long-term administration.

Thus, the tetracycline derivatives used in the present invention are effective in the treatment of articular diseases characterized by destruction of connective tissues.

These tetracycline derivatives may be administered orally, subcutaneously, percutaneously, intramuscularly or intraarticularly or by external application including nebulization (spraying) and suppository. An isomer of DOTC or DODMAT, or mixtures of 2 or more of its isomers can be administered.

The tetracycline derivatives can be formulated and prepared by established pharmaceutical procedures into compositions for administration. When such pharmaceutical compositions are intended for oral administration, they are preferably provided in dosage form suitable for absorption from the gastrointestinal tract. Tablets and capsules which are unit dosage forms for oral administration may contain binders such as crystalline cellulose, mannitol, dextrin, hydroxypropylcellulose, hydroxypropylmethylcellulose, macrogol and polyvinylpyrrolidone; excipients such as lactose, sorbitol, corn starch and calcium phosphate; lubricants such as calcium stearate and talc; disintegrators such as carboxymethylcellulose and so on. The tablets may be coated in ways known in the art.

Liquid preparations for oral administration may be aqueous or oily suspensions, solutions, syrups, elixirs and so on, or may be lyophilisates which are extemporaneously reconstituted with water or other suitable vehicles before use. Such liquid preparations may contain the usual additives inclusive of suspending agents such as sorbitol syrup, methylcellulose, glucose/sucrose syrup, gelatin, hydroxyethylcellulose, carboxymethylcellulose, aluminum stearate gel and hydrogenated edible oils and fats; emulsifiers such as lecithin, sorbitan monooleate and gum arabic; non-aqueous vehicles such as almond oil, fractionated coconut oil, oleaginous esters, propylene glycol and ethanol; preservatives such as methyl p-hydroxybenzoate, propyl p-hydroxybenzoate and sorbic acid; and so forth.

For preparing injections, the tetracycline derivative is suspended in a suitable solvent such as physiological saline and glucose solution for injection in the known manner to give injections for subcutaneous, intramuscular or intraarticular administration. In preparing the above injections, pH-adjusting agents, buffers, stabilizers, preservatives, solubilizers and so forth may be added to the aqueous solution, if necessary. For external applications, the tetracycline derivatives may be formulated into ointments, medicinal solutions, creams or the like. These formulations may incorporate diluting agents commonly used, such as animal or vegetable fat, wax, paraffin, starch, tragacanth, cellulose derivatives, polyethylene glycol, silicone, bentonite, silicic acid, talc and zinc oxide, either singly or in combination. For preparing sprays, conventional spraying agents, such as chlorofluorocarbons may be incorporated. For suppositories, a base of cacao fat, macrogol or the like is used, and further surface active agents, preservatives, fragrants, stabilizers and the like may be incorporated.

The dosage of the tetracycline derivative depends on the kind of disease, severity of the disease, patient's tolerance and other factors. However, the usual daily dosage for adult humans is, orally or by injections, 1 to 1000 mg either in a single dose or in a few divided doses. In external applications, a composition containing 0.001 to 10%, preferably 0.05 to 5% of the tetracycline derivatives is applied to the diseased part once to three times a day.

Other features of the invention will become apparent in the course of the following descriptions of exemplary embodiments which are given for illustration of the invention and are not intended to be limiting thereof.

EXAMPLES

Synthesis Example 1

Synthesis of 4-dedimethylamino-12a-deoxytetracycline (DODMAT)

A solution was prepared by dissolving 20.0 g (50 mmoles) of 4-dedimethylaminotetracycline in 500 ml of a 15% aqueous ammonia solution. To the resulting solution 40 g of zinc dust was added and the mixture was vigorously stirred. After being stirred for twenty two (22) hours, the reaction mixture was filtered to remove excess zinc dust. The filtrate was neutralized with concentrated hydrochloric acid under ice-cooling. The precipitated solid was collected by filtration, washed with water, dried, and then purified and isolated by column chromatography, to provide 3.5 g of 4-dedimethylamino-12a-deoxytetracycline (yield: 18%) as a mixture of 2 isomers. The mixture was separated by HPLC to give isomer-A and isomer-B. Their properties are shown below.

| | Isomer-A: |
|---|---|
| UV (95% EtOH) | $\lambda_{max}$ 262 nm, log $\epsilon$ 4.21, |
| | $\lambda_{max}$ 324 nm, log $\epsilon$ 4.12 |
| | Isomer-B: |
| UV (95% EtOH) | $\lambda_{max}$ 260 nm, log $\epsilon$ 4.19, |
| | $\lambda_{max}$ 362 nm, log $\epsilon$ 4.08 |

The UV absorption spectrum of isomer-A was identical to the UV absorption spectrum of DODMAT-2 described in J. Am. Chem. Soc., 82 3946 (1960). The structure of isomer-B is estimated to be the above formula DODMAT-3.

Synthesis Example 2

Synthesis of 12a-deoxytetracycline (DOTC)

A solution was prepared by dissolving 2 g of tetracycline in 50 ml of a 15% aqueous ammonia solution. To the resulting solution 4 g of zinc dust was added and the mixture was vigorously stirred. After being stirred for two (2) hours, the reaction mixture was filtered to remove excess zinc dust. The filtrate was neutralized with concentrated hydrochloric acid under ice-cooling. The precipitated solid was collected by filtration and then mixed with 450 ml of water. The mixture was adjusted to a pH of 1.8 by use of hydrochloric acid. The solution obtained was extracted with ether by liquid-liquid extraction method. The extract was concentrated to give 450 mg of crude product, which was recrystallized from dimethylformamide-methanol to yield 400 mg of 12a-deoxytetracycline (yield: 21%). HPLC revealed that this product was a mixture of two types of isomers, molecular weight FD mass [M]+428.

EXPERIMENTAL TESTS

The tetracycline derivatives used in the present invention were tested for collagenase inhibition (in vitro), and for suppression of destruction of articular cartilage using rabbit osteoarthritis models (in vivo). The test methods and the results are shown below. The tetracycline derivatives tested were the mixture of DODMAT-2 and DODMAT-3 obtained in Synthesis Example 1 (hereinafter this mixture is referred to as "DODMAT mixture" and DOTC (mixture of isomers) obtained in Synthesis Example 2. DMAT was used as control.

1. Collagenase Inhibitation Test Experiment

A. Preparation of Collagenase

The knee articular cartilage of a Japanese white rabbit (4 weeks old) was aseptically taken out. The cartilage cells (chondrocytes) were separated according to the method of S. Collier et al [Ann. Rheum. Dis., 48, 372 (1989)]. In 30 ml of Ham's F12 culture medium (containing 10% fetal bovine serum) $4 \times 10^6$ cartilage cells were suspended and the medium was incubated at 37° C. in a 150 cm$^2$ incubation flask (made by Iwaki Glass Co., Japan) and under an air atmosphere containing 5% carbon dioxide. The medium was replaced every 3 to 4 days. When the cells propagated to the state of confluence (7 to 9 days after the start of incubation), the medium was replaced by Ham's F12 serum-free culture medium (30 units/ml of human recombinant Interleukin-1a made by Genzyme Co., USA) and 0.4% lactalbumin hydrolysate (made by Sigma Co., USA) and incubation was conducted for 4 days. The culture supernatant was taken and used as the collagenase solution to be tested.

B. Measurement of Collagenase Activity

The above collagenase solution was activated by treating with trypsin according to the method of Nagai et al [Ensho, 4, 247 (1984)], and then the trypsin added was deactivated with soybean trypsin inhibitor (made by Sigma Co.) to obtain activated collagenase solution. The collagenase activity was measured according to the method of Nagai et al [Ensho, 4, 123 (1984)], which comprises measuring decomposition activity of FITC-labelled collagen. The collagenase activity was expressed based on the decomposition of 1 μg of collagen at 35° C. in 1 minute being equal to 1 unit.

C. Activity of Collagenase Inhibition

A solution of a drug to be tested was dissolved in dimethyl sulfoxide (DMSO), then was added to the collagenase assay solution. The final concentration of DMSO is 5%. The inhibition ratio of the drug was calculated based on the collagen decomposition activity without its addition being 100%.

The results are shown in Table 1.

TABLE 1

| Drug tested | Concentration of Drug Showing 50% Inhibition, IC$_{50}$ (M) |
|---|---|
| DODMAT mixture | $2.5 \times 10^{-6}$ |
| DOTC obtained in Synthesis Example 2 | $2.2 \times 10^{-5}$ |
| DMAT | $3.0 \times 10^{-4}$ |

As is apparent from Table 1, the DODMAT mixture and DOTC obtained in Synthesis Example 2 both were confirmed to have collagenase inhibition activity as strong as at least 10 times that of DMAT.

2. Test for Suppression of Destruction of Articular Cartilage Using Rabbit Osteoarthritis Models

A. Preparation of Rabbit Osteoarthritis Models

The rabbit osteoarthritis models were made by the partial lateral meniscectomy procedure according to the method of C. Colombo et al [Arthritis Rheum., 26, 875 (1983)]. Adult male New Zealand white rabbits weighing approximately 3 kg each were used. The animals were anesthetized by intramuscular injection of 40 mg/kg Ketamine and 1.6 mg/kg Xylazine before surgery. The surgery was conducted as follows; the right knee was opened laterally, the fibular collateral ligament was exposed and 3-4 mm were removed. Subsequently, 3-4 mm of the sesamoid ligament were removed, followed by removal of 4-5 mm of the anterior lateral area of the exposed meniscus. The capsule and skin were then sutured. Following surgery, each animal daily received intramuscular injection of 2 mg/kg/day Dibekacin sulfate for a week to be protected from infection. The animals were sustained on standard rabbit pellets and tap water ad libitum during experiment.

B. Test for Suppression of Destruction of Articular Cartilage

The test drug (DODMAT mixture) or vehicle began 1 week post-surgery and continued every 7 days per week for 5 weeks. DODMAT, suspended in a vehicle aqueous solution containing 1% methyl cellulose, 0.8% sodium chloride, and 0.1% polysorbate 80, was administered orally by gavage. At 6 weeks after the surgery, the animals were killed, and the samples of femoral cartilage of operated (right) and control (left) knees were obtained and either fixed immediately in a solution containing 20% formalin and 20% methanol for a week, followed by complete decalcification in 0.5M EDTA solution (pH 7.5). Each femoral sample was taken as three cross-sections; one was obtained along an imaginary line from the center of the joint through the lateral condyle, and the other two were obtained along parallel lines with interval of 5 mm on both sides of the former one. The sections were stained with Safranin O-Fast Green for the histological evaluation. The samples from left knees served as normal controls for the evaluation of destruction of articular cartilage of right knees. The histologic slides were coded and evaluated blind for 11 parameters, which are set forth in Table 2, using a scoring system of +1 to +4 for each type of abnormality as described by C. Colombo et al [Arthritis Rheum., 26, 875 (1983)]. Scores of the three sections from one femoral cartilage sample were combined. The data were analyzed by the one-sided Wilcoxon rank sum method. The results are shown in Table 3.

TABLE 2
Parameters for Scoring Abnormalities in Articular Cartilage of Rabbit Knee Joints Following Lateral Meniscectomy

| Articular cartilage abnormalities | Scores | | | |
|---|---|---|---|---|
| | +1 | +2 | +3 | +4 |
| Loss of superficial layer | Slight | Moderate | Focally severe | Extensively severe |
| Ulceration of erosion | Detectable | Moderate | Focally severe | Extensively severe |
| Fibrillation (surface fragmentation) | Noticeable | Moderate | Marked | Extensive |
| Fissures ("V"-shaped clefts) | 1 very small | 1 small | 2 small or 1 medium | 3 small, 2 medium, or 1 large |
| Cysts | 1 very small | 1 small | 2 small or 1 large | 3 small or 2 large |
| Osteophytes/chondrophytes | Very small | Small | Medium | Large |
| Loss of stainable proteoglycan | Paler stain than control | Moderate loss of safraninophilia | Marked loss of safraninophilia | Total loss of safraninophilia |
| Disorganization of chondrocytes | Noticeable | Moderate, with some loss of columns | Marked loss of columns | No recognizable organization |
| Clones* | 3-4 small or 1-2 medium or 1-2 large | 5-6 small, 3-4 medium or 1-2 large | 7 or more small, 5-6 medium or 3-large | 7 or more medium or 5-6 large |
| Loss of chondrocytes | Noticeable decrease in cells | Moderate decrease in cells | Marked decrease in cells | Very extensive decrease in cells |
| Exposure of subchondral bone | Focal Exposure of bone | Moderate exposure of bone | Fairly extensive exposure of bone | Very extensive exposure of bone |

*Small = 2-4 cells; medium = 5-8 cells; large = 9 or more cells.

TABLE 3
Effect of DODMAT on destruction of articular cartilage in rabbit osteoarthritis models

| Tested Compound | Dose (mg/kg/day) | No. of animals | Mean score of cartilage lesions ± S.E. | Statistical analysis |
|---|---|---|---|---|
| Vehicle | — | 7 | 46.6 ± 7.3 | — |
| DODMAT | 15 | 9 | 24.7 ± 3.3 | $p < 0.05$ |

These results show at least about 47% improvement resulting from treatment of DODMAT.

EXAMPLES OF COMPOSITIONS FOR DELIVERY OF ACTIVE

Formulation Example 1

| Tablets | |
|---|---|
| DODMAT mixture | 100 g |
| Corn starch | 80 g |
| Carboxymethylcellulose | 15 g |
| Polyvinylpyrrolidone | 3 g |
| Calcium stearate | 2 g |
| Total | 200 g |

The above formulation was mixed to form a powder from which tablets each weighing 200 mg were prepared. Each tablet contained 100 mg of the DODMAT mixture.

Formulation Example 2

| Powder and capsule | |
|---|---|
| DODMAT mixture | 100 g |
| Crystalline cellulose | 100 g |
| Total | 200 g |

The two powders set forth in Formulation Example 2 in the above Table were mixed to make a powder drug. The powder drug was placed into hard No. 3 capsules to form a capsule delivery system.

Obviously, numerous modifications and variations are possible in light of the above teachings. It is therefore to be understood that within the scope of the appended claims the invention may be practiced otherwise than as specifically described herein.

What is claimed is:

1. A method for treating humans or animals suffering from a condition or disease characterized by excessive collagen destruction, which comprises administering to said human or animal an effective amount of a 12a-deoxytetracycline represented by the following general formula (1)

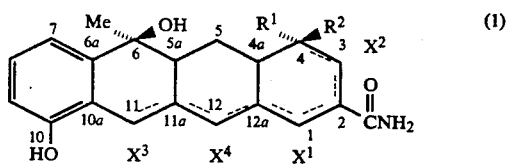

wherein $R^1$ represents a hydrogen atom or a dimethylamino group, $R^2$ represents a hydrogen atom or forms a double bond with the carbon atom in the C-3 position, $X^1$, $X^2$, $X^3$ and $X^4$ each represents a hydroxyl group or an oxo group and the broken lines drawn in places mean that there may be present a carbon-carbon double bond or a double bond formed by $X^1$, $X^2$, $X^3$ or $X^4$ and a ring-forming carbon atom in each of the places, the number of the bonds present in the places of the broken lines being 4 with the following conditions:

where $X^1$ represents a hydroxyl group, either one of C12a-C1 bond or C1-C2 bond is a double bond;

where $X^2$ represents a hydroxyl group, either one of C2-C3 bond or C3-C4 bond is a double bond;

where $X^3$ represents a hydroxyl group, C11-C11a is a double bond and where $X^4$ represents a hydroxyl group, either one of C11a-C12 bond or C12-C12a bond is a double bond; with the limitation that said C1-C2 bond and said C2-C3 bond, said C11-C11a bond and said C11a-C12 bond or said C12-C12a bond and C12a-C1 cannot be double bonds at the same time; and where $X^1$ represents an oxo group, said C12a-C1 bond and C1-C2 bonds are each a single bond, where $X^2$ represents an oxo group, said C2-C3 bond and C3-C4 bond are each a single bond, where $X^3$ represents an oxo group, said C11-C11a bond is a single bond, and where $X^4$ represents an oxo group, said C11a-C12 bond and C12-C12a bond are each a single bond;

or its pharmaceutically acceptable salts.

2. A method according to claim 1, wherein said 12a-deoxytetracycline is a 4-dedimethylamino-12a-deoxytetracycline.

3. A method according to claim 1, wherein said 12a-deoxytetracycline is a mixture of two compounds represented by the following two formulas respectively

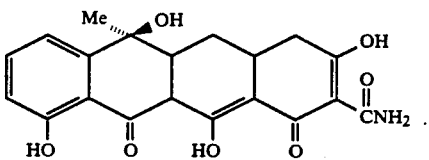

and

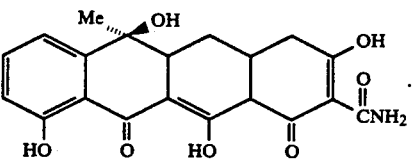

4. A method according to claim 1, wherein said diseases characterized by excessive collagen destruction are articular diseases.

5. A method according to claim 4, wherein said articular diseases are rheumatoid arthritis and osteoarthritis.

* * * * *

UNITED STATES PATENT AND TRADEMARK OFFICE
CERTIFICATE OF CORRECTION

PATENT NO. : 5,258,371
DATED : November 2, 1993
INVENTOR(S) : Golub, et al.

It is certified that error appears in the above-identified patent and that said Letters Patent is hereby corrected as shown below:

TITLE PAGE: The Assignee should correctly read: "The Research Foundation of State University of New York, Albany, N.Y.; Kuraray Co., Ltd., Osaka, Japan ITEM [73]: should read: "The Research Foundation of State University of New York, Albany, N.Y.; Kuraray Co., Ltd., Osaka, Japan Signed and Sealed this Twentieth Day of September, 1994

BRUCE LEHMAN

Attest:

Attesting Officer     Commissioner of Patents and Trademarks